US012761220B2

(12) United States Patent
Tanaka

(10) Patent No.: US 12,761,220 B2
(45) Date of Patent: Oct. 13, 2026

(54) SUBSTANCE DETECTION DEVICE

(71) Applicant: RIKEN, Wako (JP)

(72) Inventor: Takuo Tanaka, Saitama (JP)

(73) Assignee: RIKEN, Saitama (JP)

( * ) Notice: Subject to any disclaimer, the term of this patent is extended or adjusted under 35 U.S.C. 154(b) by 751 days.

(21) Appl. No.: 18/258,540

(22) PCT Filed: Dec. 16, 2021

(86) PCT No.: PCT/JP2021/046643
§ 371 (c)(1),
(2) Date: Jun. 20, 2023

(87) PCT Pub. No.: WO2022/138470
PCT Pub. Date: Jun. 30, 2022

(65) Prior Publication Data
US 2024/0036040 A1 Feb. 1, 2024

(30) Foreign Application Priority Data
Dec. 21, 2020 (JP) ................................ 2020-211894

(51) Int. Cl.
*G01N 33/543* (2006.01)
*B01L 3/00* (2006.01)
*G01N 33/553* (2006.01)

(52) U.S. Cl.
CPC .. *G01N 33/54386* (2013.01); *B01L 3/502761* (2013.01); *G01N 33/553* (2013.01);
(Continued)

(58) Field of Classification Search
CPC ......... B01L 2200/0668; B01L 2200/16; B01L 2300/0654; B01L 2300/168;
(Continued)

(56) References Cited

U.S. PATENT DOCUMENTS

2018/0202918 A1 7/2018 Tanaka et al.

FOREIGN PATENT DOCUMENTS

JP 2000055920 A 2/2000
JP 2015514225 A 5/2015
(Continued)

OTHER PUBLICATIONS

Fujifilm begins development of a highly sensitive and rapid antigen test kit for new coronaviruses, applying silver halide amplification technology for photographic development Oct. 5, 2020, Inner Vision Ltd, https://www.innervision.co.jp/sp/products/release/20201115, [online], Last Visited: Dec. 2, 2020.
(Continued)

*Primary Examiner* — Kathryn Elizabeth Limbaugh
(74) *Attorney, Agent, or Firm* — Seed Intellectual Property Law Group LLP

(57) ABSTRACT

Provided is an easy to determine immunochromatography detection device that detects a target substance that may be contained in a sample fluid. The detection device includes a flow path for the sample fluid and detection parts 1 to which capture selected substances. In one embodiment, an Metal-Insulator-Metal (MIM) structure is formed when the target substance is included in the sample fluid at the detection parts, and a color is produced at the detection parts by resonance absorption. The MIM structure comprises a metal thin film (M layer) that is formed on a support that acts as either a capture substance/target substance/reference substance composite layer or a capture substance/reference substance composite layer (I layer), and metal fine particles (M layer) with which a reference substance is labeled.

14 Claims, 10 Drawing Sheets

(52) U.S. Cl.
CPC ... *B01L 2200/0668* (2013.01); *B01L 2200/16* (2013.01); *B01L 2300/0654* (2013.01); *B01L 2300/168* (2013.01)

(58) Field of Classification Search
CPC ........ B01L 3/502761; G01N 33/54386; G01N 33/54388; G01N 33/553; G01N 33/588
See application file for complete search history.

(56) References Cited

FOREIGN PATENT DOCUMENTS

| | | | |
|---|---|---|---|
| JP | 2019219272 | A | 12/2019 |
| WO | WO 2008078579 | A1 | 7/2008 |
| WO | WO 2009072441 | A1 | 6/2009 |
| WO | WO 2012043746 | A1 | 4/2012 |
| WO | WO 2016132979 | A1 | 8/2016 |
| WO | WO 2017010411 | A1 | 1/2017 |
| WO | WO 2020066369 | A1 | 4/2020 |
| WO | WO 2022138470 | A1 | 6/2022 |

OTHER PUBLICATIONS

Nagasaki et al., "All-Dialectric Dual-Color Pixel with Subwavelength Resolution," *Nano Letters* 17: 7500-7506, 2017.
Okamoto, "Gold Nanoparticles, in Lecture Course of Nanoparticle, 2," *Kagaku-To-Kyoiku* (*Chemistry and Education*) *56:3, The Chemical Society of Japan*, Mar. 20, 2008.
Tanaka et al., "A novel enhancement assay for immunochromatographic test strips using gold nanoparticles," *Anal Bional Chem* 385: 1414-1420, 2006.
Uehara et al., "Sensing System Based on Plasmonic Properties of Gold Nanoparticles," *Bunseki 12, The Japan Society for Analytical Chemistry*, Dec. 5, 2010. (9 pages).
Uehara, "Polymer-functionalized Gold Nanoparticles as Versatile Sensing Materials," The Japan Society for Analytical Chemistry, Analytical Sciences 26: 1219-1228, Dec. 10, 2010.
Wada et al., "The Novel Technology for Highly Sensitive Immunochromatography," *The Japan Society for Analytical Chemistry, Bunseki* 530, Feb. 2019. (9 pages).
Extended European Search Report, dated Oct. 4, 2024, for European Patent Application No. 21910618.4. (12 pages).
Song et al., "Imprinted gold 2D nanoarray for highly sensitive and convenient PSA detection via plasmon excited quantum dots," Lab Chip 15(1):253-263, Oct. 16, 2014. (11 pages).
Okamoto, "Gold nanoparticles (Course: Nanoparticles 2)," *Chemistry and Education* 56(3):132-135, Mar. 20, 2008.

FIG. 10A Au / Al (100nm) / Si
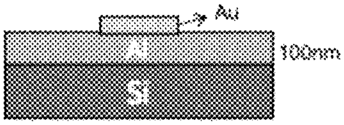
FIG. 10B
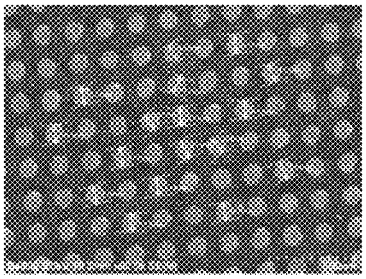
FIG. 10C
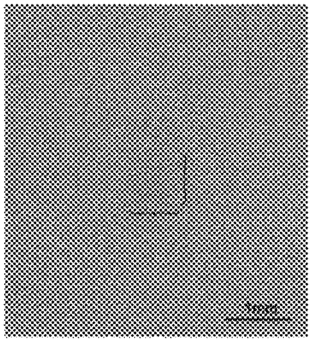
FIG. 10D
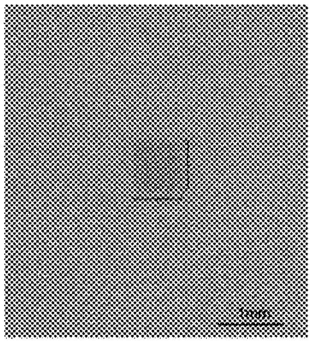

SUBSTANCE DETECTION DEVICE

BACKGROUND

Technical Field

The present disclosure relates to a substance detection device. More particularly, the present disclosure relates to a substance detection device that utilizes a phenomenon of resonant absorption originating from a light-absorbing nanostructure.

Description of the Related Art

An antigen detection method called "immunochromatography," which uses a reference antibody labeled with a gold colloid, enzyme, or fluorescent molecule that binds specifically to a particular antigen, and a capture antibody that binds to it, has been developed (for example, Patent Document 1). More recently, a test kit for antibodies against the novel coronavirus (SARS-CoV-2), the virus of novel coronavirus infections (COVID-19), has also been developed (for example, Non-Patent Document 1).

The inventor, on the other hand, has previously developed a visible light absorption device (Patent Document 2). Also, a plasmon resonance measurement system has been disclosed (Patent Document 3). Furthermore, it has been disclosed that Si fine particles can be a chromophore by itself (Non-Patent Document 2).

CITATION LIST

Patent Documents

Patent Document 1: WO2012/043746
Patent Document 2: WO2016/132979
Patent Document 3: JP 2019-219272 A

Non-Patent Documents

Non-Patent Document 1: "FUJIFILM begins development of a highly sensitive and rapid antigen test kit for new coronaviruses, applying silver halide amplification technology for photographic development" Oct. 5, 2020, INNERVISION LTD, https://www.innervision.cajp/sp/products/release/20201115, [online], Last Visited: Dec. 2, 2020

Non-Patent Document 2: Yusuke Nagasaki, Masafumi Suzuki, and Junichi Takahara, "All-Dielectric Dual-Color Pixel with Subwavelength Resolution", Nano Letters 17, pp. 7500-7506 (2017); DOI: 10.1021/acs.nanolett.7b03421

BRIEF SUMMARY

The inventor has realized that conventional test kits based on the immunochromatography technique, kits using fluorescent molecules labeling require a dedicated light source and photographic equipment to observe the fluorescent emission. In addition, in immunochromatography kits using gold colloids labeling, the pink color produced by the gold colloids is observed visually. In this case, if the amount of antibodies or the like is minute, a scanner is required to photograph the faint color with high sensitivity, making it difficult for ordinary users to use such test kits conveniently at home. To deal with this problem, a method has been previously proposed in which the faint color of gold colloids is enhanced by reducing silver ions on the surface of gold nanoparticles for amplifying the size of gold fine particles by about 100 times, thereby increasing visual detection capability (silver amplified immunochromatography method, Non-Patent Document 1). However, the inventor has realized that this sensitization process using silver ions has not yet solved the problem of not being easily accessible to the general public, as it requires dedicated equipment for the process.

The present disclosure addresses both of the above issues and provides and teaches a detection device that can be easily used by general users, thereby contributing to popularization of testing technology to be used for determining the presence or absence of a target substance.

The inventor conceived a new idea in which a color in the visible range is used to enable detection of the target substance based on antigen-antibody reactions, a type of physicochemical binding. Specifically, we adopt structures of color developing elements employing light-absorbing nanostructures for combining with the immunochromatography method. By employing the coloring phenomenon derived from the light-absorbing nanostructure, it would be possible to indicate the presence or absence of a target substance (e.g., antigen) in an analyte by way of change in color that is sensitively detectable by vision. The inventor has found that the detection device based on this concept can greatly enhance the practicality of tests using antigen-antibody reactions or the like, and has completed the disclosure in the present application.

Therefore, provided in this disclosure is a detection device for detecting a target substance that may be contained in a sample fluid comprising: a flow path for the sample fluid to which a reference substance is dispersed, the reference substance being capable of physicochemically binding to the target substance, and at least one detection part disposed in the flow path, the detection part being visible and having a capture substance fixed to at least part of a contact surface thereof against the sample fluid, wherein the reference substance is labeled by fine particles, wherein the capture substance can bind physicochemically at least either to the target substance that is bound to the reference substance, or to the reference substance, and wherein the fine particles form an assembly along the contact surface and produce a color, the assembly being formed by the physicochemical binding of the target substance, which binds to the reference substance, to the capture substance, or by the physicochemical binding of the reference substance to the capture substance.

In this application, the target substance is typically a molecule or an antigen such as a protein component of a virus, or in another typical case, an antibody. In the case when the target substance is the protein component of a virus, other molecule, or antigen, a reference substance or a capture substance that physicochemically binds to the target substance is typically an antibody. In the case when the target substance is an antibody, the reference or capture substance that physicochemically binds to the target substance is typically an antigen. Furthermore, in the description of this application, a change in color includes any optical change that a human with normal color vision can detect through his or her vision, including a change in hue, lightness or darkness, transmittance, or reflectance as examples, and further including visibly highlighting of some pattern or mark according to such changes. For this reason, coloration or color presentation includes any response of an object to visible light, where the response might result in at least some stimulation to the observer's vision itself or modulation of the amount of such stimulation. The response may include any response that invokes change in at least one of lightness, darkness, hue, or saturation. The description of antigen-antibody reactions in this disclosure is primarily based on the case where the sample fluid is the analyte (sample) and the antigen contained therein is the detection target. However, as is clear to those skilled in the art, the antigen-antibody reaction described in this disclosure can also be realized by exchanging the antigen with the antibody, and the contents of this disclosure include the case where the antibody serves as the detection target. The physicochemical binding is typically a selective binding reaction that has specificity to the combination of substances, such as the antigen-antibody reaction of immunological reactions.

Fine particles in this disclosure are mainly nano-order sized fine particles of materials that can behave as a dielectric or a metallic material in response to the electric or magnetic field of electromagnetic waves in the wavelength range included in a visible light. Typical examples of their particle size are about 400 nm or less. When such fine particles form an assembly of themselves, they may exhibit a physical-optical effect. The physical-optical effects exhibited by the assembled fine particles are modified ones to at least some degree from the ones exhibited by non-assembled fine particles alone. An MIM structure in the present disclosure is a structure having at least three layers of metal-insulator-metal, (aka, metal-dielectric-metal) ("MIM"), wherein the dielectric layer is configured to have a material and thickness that allow at least some transmission of electromagnetic waves in the visible region. It is not necessary that all the layers of the MIM structure be recognized as membranes or thin films in the usual sense. For example, the present disclosure describes one in which either of the M layers in the MIM structure is composed of an assembly of metal fine particles. In this disclosure, the optical changes to be detected, the device structure, and the function may be described using technical terms adopted or borrowed from any technical field in which changes in hue or lightness or darkness in visible light are described.

In the detection device provided in any of the aspects of the present disclosure, the presence of an antigen including a molecule such as a protein component of a virus can be indicated as a change in color of the device. In any of the aspects of the present disclosure, it is possible to quickly and easily determine or guess via vision whether the target antigen is present in the analyte by means of a change in the color of the device, simply by placing a drop or drops of the analyte sample on the detection device.

BRIEF DESCRIPTION OF THE SEVERAL VIEWS OF THE DRAWINGS

FIG. 10A is a schematic cross-sectional view illustrating the conditions for experimentally verifying the operational principle of a detection device of an embodiment of the present disclosure;

FIG. 10B is an SEM photograph of a gold pattern formed actually; and

FIGS. 10C and 10D are optical microscope images before and after the sample fluid was deposited, respectively.

DETAILED DESCRIPTION

Figures 1A, 1B:
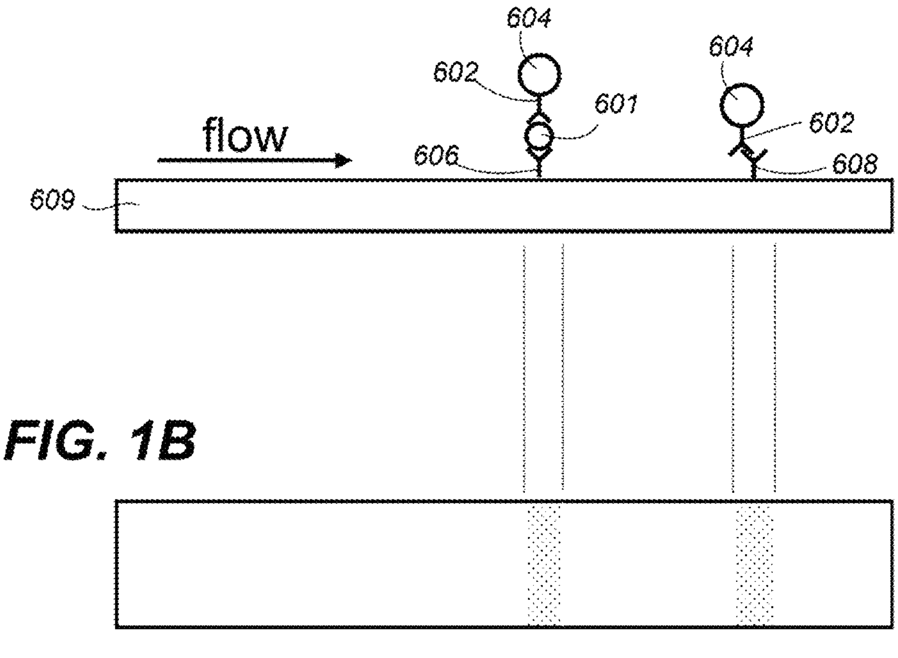
FIG. 1A is a schematic cross-sectional view illustrating the principle of a conventional immunochromatography technique using gold colloidal labeling.
FIG. 1B is a schematic plan view illustrating the principle.

In the following, a detection device according to the present disclosure will be described. In the description below, for the purpose of clearly explaining the disclosure, the sample fluid is primarily used for the analyte (sample), primarily assuming that an antigen contained therein is the target of detection. However, as will be clear to those skilled in the art, the antigen-antibody reaction described in this disclosure can also be realized by exchanging the antigen with the antibody. It can also be applied to a pair of molecules that identify and bind to each other in the same way. Throughout the drawings, common parts or elements are denoted by common reference numerals in this description, unless otherwise noted. In addition, each element of each embodiment in the drawing should be understood as not being drawn to scale.

1. OVERVIEW

The detection device provided in this disclosure will be described by contrasting it with ones for the conventional immunochromatography technique that utilize gold colloidal labeling. FIG. 1A is a schematic cross-sectional view illustrating the principle of a conventional immunochromatography technique using gold colloidal labeling, and FIG. 1B is a schematic plan view illustrating the principle. In this conventional technique, the reference antibody 602, which is labeled with gold nanoparticles 604, is placed in a pre-releasable position, not shown, where it comes into contact with the liquid analyte sample. The position is, for example, where the analyte is dropped or an adjacent position to which the analyte can be reached, and is referred to as a conjugate section. The gold nanoparticles 604 become colloidal when dispersed alone in a medium such as water, which will also have the same properties when the reference antibody 602 is labeled with them. The analyte sample that comes into contact with the reference antibody 602 passes by diffusion, osmosis, or capillary action down a substrate 609 such as a cellulose membrane, while the reference antibody 602 labeled with gold nanoparticles 604 is dispersed in a colloidal form. The substrate that forms the flow path for the passage serves as the chromatographic medium, on which the capture antibodies A606 and B608 are situated spaced apart with each other. The positions of the capture antibodies A606 and B608 are the test part and the control part, respectively. In many examples, the test and control parts are arranged upstream and downstream in this order, to form lines of visible size crossing the flow path through which the analyte passes.

In the conventional immunochromatography technique employing labeling with gold nanoparticles, in the case where the analyte contains the target antigen 601, the antigen is dispersed in the analyte as a result of an antigen-antibody reaction, in which the antigen is bound to a reference antibody 602 labeled with gold nanoparticles 604. In contrast, in the case where the analyte that does not contain a target antigen 601, no antigen-antibody reaction occurs, as a result, the reference antibody 602 labeled with gold nanoparticles 604 is dispersed without binding to the antigen 601. When the analyte contains the antigen 601 but its amount is small, excess amount of the reference antibody 602 also is dispersed without binding to the antigen 601. The analyte passes through the flow paths in which a capture antibody A606 in the test part and a capture antibody B608 in the control part are arranged in this order, by diffusion, osmosis, capillary action, etc. As for a conjugate of the antigen 601 and the reference antibody 602 in the analyte, the antigen portion of the conjugate binds to capture the antibody A606 placed in the test part in the upstream side by the antigen-antibody reaction. In contrast, the reference antibody that has not bound to the antigen in the analyte can bind to the capture antibody B608 located in the control part in the downstream side by an antigen-antibody reaction, but it cannot bind to the capture antibody A606 in the upstream side. The reference antibody 602 produces a pink color as it is labeled by gold nanoparticles 604, as a result of the absorption of green light associated with surface plasmon resonance.

In the conventional immunochromatography technique employing labeling with gold nanoparticles, when the position of the downstream control part (capture antibody B608) turns pink while the upstream test part (capture antibody A606) remains colorless, then it is judged that the analyte does not contain the antigen 601. When two pink bands appear, one at the test part and the other at the control part, it is judged that the analyte actually contained the antigen 601 (i.e., it was positive). When only the test part is colored, or if both the control and test parts are colorless, the test is considered defective. In all cases, the pink color is produced as a result of surface plasmon resonance of each individual gold nanoparticle 604 itself.

Figure 2:
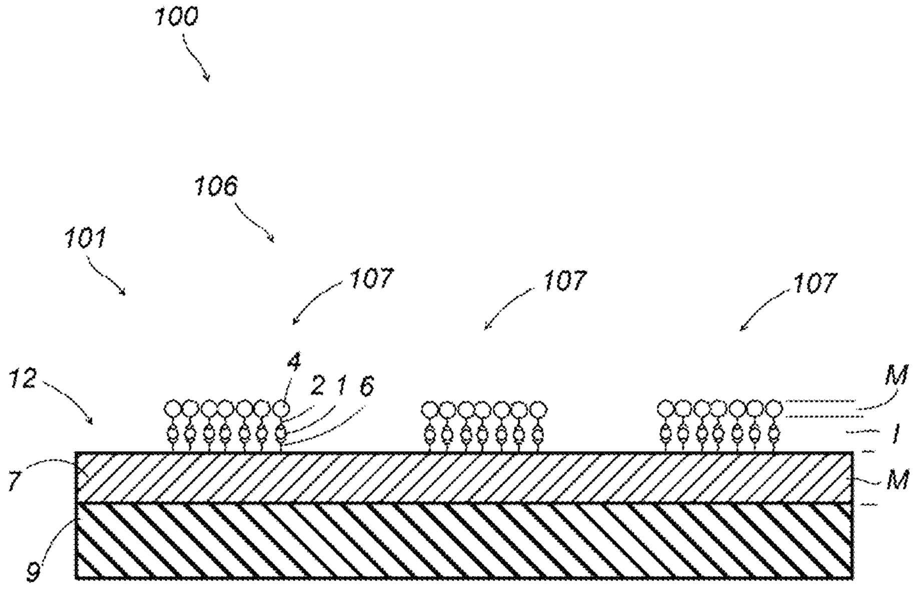
FIG. 2 is a diagram illustrating the basic principle of the improved immunochromatography method in an embodiment of the present disclosure, which employs a configuration of an MIM structure.

FIG. 2 is a diagram illustrating the basic principle of the improved immunochromatography method in the present embodiment, which employs a configuration of an MIM structure. For the present disclosure, we utilize coloring phenomenon in which a color of the color developing elements is changed at least from one produced by the fine particles alone, due to the fact that the fine particles form an assembly. The basic principle is explained here with an example having a metal-(transparent) dielectric material-metal (Metal-Insulator-Metal, or hereinafter "MIM") structure, in which one metal layer is composed of an assembly of metal fine particles. Namely, in a typical detection device 100 of this embodiment, a metal thin film 7 is formed for coloring in a flow path 101 for the passage of the analyte beforehand on a substrate 9. This flow path 101 is any flow path in which the sample fluid 12 can spread for a chromatographic medium as an example, but the properties of the flow path may be modified by forming the metal thin film 7. It is the test part 106 and the control part that produce colors, while FIG. 2 illustrates the test part 106 only. The surface of the metal thin film 7, or the surface with capture antibodies along that surface, is the contact surface against which the sample fluid 12 contacts. The test part 106 and the control part are sometimes collectively referred to as a detection part in this disclosure. In the test part 106, the antigen 1, which has already bound to the reference antibody 2 in the sample fluid 12 due to an antigen-antibody reaction (antigen-antibody interaction), and the capture antibody 6, which is located there, further bind to each other by an antigen-antibody reaction. As a result, the spreading metal thin film 7 and the assembly of appropriate metal fine particles 4 labeling the reference antibody 2 form an MIM structure sandwiching a composite layer of the reference antibody 2—antigen 1—capture antibody 6 between them. The assembly of metal fine particles 4 is formed along the spread of the above contact surface. The insulator is in the form of a dielectric body. A layer corresponding to the dielectric body located between the two metal layers is a single or multiple layers showing an optical function of translucency with weak absorption, and is referred to as a transparent dielectric layer. In the test part 106, colors affected by the absorption characteristics of the MIM structure are visually observed. On the other hand, the reference antibody 2, which has not reacted with the antigen 1, is not captured by the capture antibody 6 in the test part 106 as it has not bound to the antigen 1, and therefore does not form an MIM structure in the test part 106. In this case, the test part 106 remains the background color of the metal thin film 7 formed on the substrate 9. This may be described as producing no color or exhibiting no color in the present embodiment. In a typical example, the capture antibody 6 or the like is patterned in such a manner that islands 107 will be made after the MIM structure is formed, and the shape, arrangement, and size of the pattern determines the wavelength characteristics, or color tone, of the resonance absorption. This is because the optical properties exhibited by the assembly of the metal fine particles 4 change due to the patterning of the capture antibody 6.

Figure 3:
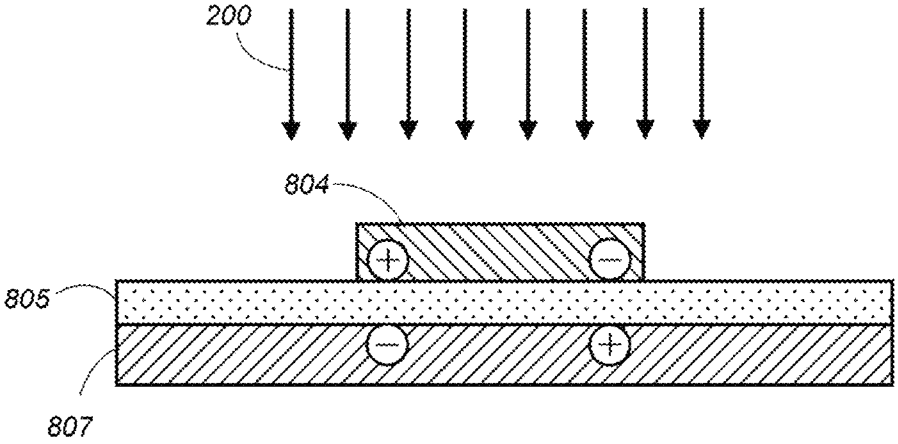
FIG. 3 is a diagram illustrating the resonance phenomenon in an MIM structure in a general setting.

Specifically, the detection device of the present disclosure that employs the MIM structure has the advantage that this absorption characteristic can be changed artificially by designing the shape, arrangement, and size of the patterns mentioned above, as well as the thickness and dielectric properties of the dielectric layer. FIG. 3 is a diagram illustrating the resonance phenomenon in an MIM structure in a general setting. When the MIM structure is irradiated with illumination light 200, such as in a room, free electron oscillations are induced in the upper metal structure 804 in response to the electromagnetic waves, and free electron oscillations, which are a mirror image of those oscillations, are also induced in the lower metal thin film 807. Since electromagnetic waves are radiated from each of the oscillations of electrons, the electromagnetic waves can be made to cancel each other out and weaken in the reflection direction toward the top of the paper, which is the observation direction, by adjusting the thickness and characteristics of the transparent dielectric layer 805. That is, interference that weakens the electromagnetic waves can occur. On the other hand, the illumination light 200 cannot travel through the lower metal thin film 807. The energy of the light that cannot either be reflected or transmitted is caught between the two metal layers and is eventually absorbed by the metal of the upper metal structure 804 or the lower metal thin film 807 which turns it into heat. This phenomenon is wavelength dependent because it is based on interference of waves. This allows the MIM structure to function as an absorber of light, and its wavelength dependence can be tuned by the geometrical and material properties. The geometrical properties that affect the wavelength dependence typically include the shape and size of the overlap between the upper metal structure 804 and the lower metal thin film 807, the distance between the islands if the upper metal structure 804 has a repeat pattern of islands, such as the islands 107 in FIG. 2, and thickness of the transparent dielectric layer 805. The material properties that affect wavelength dependence include the frequency response (dielectric function) of the dielectric properties of the upper metal structure 804, the lower metal thin film 807, and the transparent dielectric layer 805. The general method of artificially designing colors by adjusting the geometry and materials as described above has been developed by the inventor (for example, Patent Document2). In the detection device employing the MIM structure in the present disclosure, the pattern corresponding to the upper metal structure 804 is realized by the assembly of the metal fine particles 4 in the islands 107 (FIG. 2). Therefore, the color of the detection device 100 can be produced with an artificial modification from the color of the metal fine particles 4 themselves.

Figure 4:
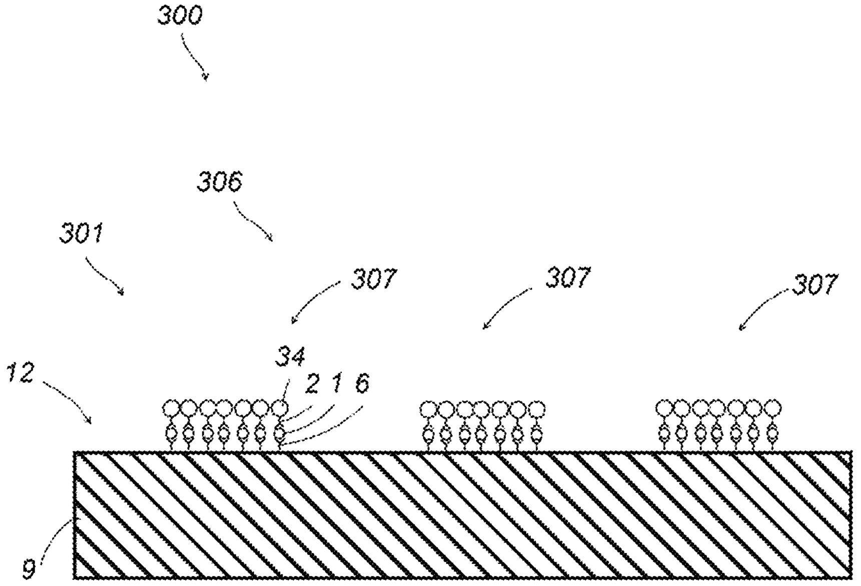
FIG. 4 is a diagram illustrating the basic principle of the improved immunochromatography method in the embodiment of the present disclosure, which employs a color by an assembly of fine particles.

In addition to those employing the MIM structure, the present disclosure also provides a detection device employing color developing elements having assembly of fine particles. FIG. 4 is a diagram illustrating the basic principle of the improved immunochromatography method in the present embodiment, which employs producing a color by an assembly of fine particles. The substrate 9 of the detection device 300 can be made of any material and can be of any structure. For example, the substrate 9 can be provided with any patterning means to fix the capture antibody 6 only in a predetermined area. Therefore, the surface of the substrate 9, or the surface with the capture antibody 6 along its surface, is the contact surface against which the sample fluid 12 contacts. If another layer is formed on the surface of the substrate 9, the surface of that other layer will be the contact surface. The detection device 300 does not necessarily require a metal thin film in the flow path 301 for the passage of the analyte, and this flow path 301 is also an arbitrary flow path in which the sample fluid 12 can be deployed. The test part 306 and the control part are the ones that will be colored, and only the test part 306 is shown in FIG. 4. In the test part 306, the antigen 1, which is bound to the reference antibody 2 in the sample fluid 12, and the capture antibody 6, which is located there, further combine due to an antigen-antibody reaction. As a result, the assembly of the fine particles 34, which label the reference antibody 2 and form the assembly along the spread of the contact surface mentioned above, will develop a color in accordance with the size and shape of the assembly. At the test part 106, the color corresponding to the absorption characteristics of the assembly of the fine particles 34 is visually observed. The absorption characteristics of the assembly of the fine particles 34 vary with the shape and size of the islands 307, in addition to the shape, dielectric properties in the optical domain, and size of the individual fine particles 34.

One suitable type of fine particles 34 is semiconductor fine particles. Preferred semiconductor materials for the semiconductor fine particles for the fine particles 34 include any one selected from the group consisting of silicon (Si), germanium (Ge), and gallium (Ga). Another type of material suitable for fine particles 34 is compound fine particles. Preferred compound materials for the fine particles 34 include any one selected from the group consisting of titanium nitride (TiN), silicon carbide (SiC), gallium nitride (GaN), hafnium sulfide ($HfS_2$), zinc sulfide (ZnS), barium titanate ($BaTiO_3$), and vanadium dioxide ($VO_2$). When the fine particles 34 are compound fine particles, properties of the material of the fine particles 34 that are required for the assembly of the fine particles 34 to properly develop a color are generally a large dielectric constant or a significant imaginary part of the refractive index.

The color of the detection device 300 can also be adjusted from a color shown by the assembly of the fine particles 34. One suitable technique in this respect is to form a thin metal film (not shown) on the substrate, thereby employing the same structure for the substrate of the detection device 300 as the laminate of the substrate 9 and the metal thin film 7 shown in FIG. 2. In that structure, the metal thin film formed, together with the assembly of the fine particles 34, will have a structure that sandwiches the composite layer of the reference antibody 2—antigen 1—capture antibody 6 between them. Namely, in terms of the MIM structure (FIG. 2), the lower M layer corresponds to the metal thin film, whereas the layer corresponding to the upper M layer is the assembly of the fine particles 34, which are not necessarily metal. The response of the assembly of the fine particles 34 in such a structure to visible light can be modulated by the metal thin film.

2. STRUCTURE DETAILS

Figures 5A, 5B, 5C, 5D, 5E:
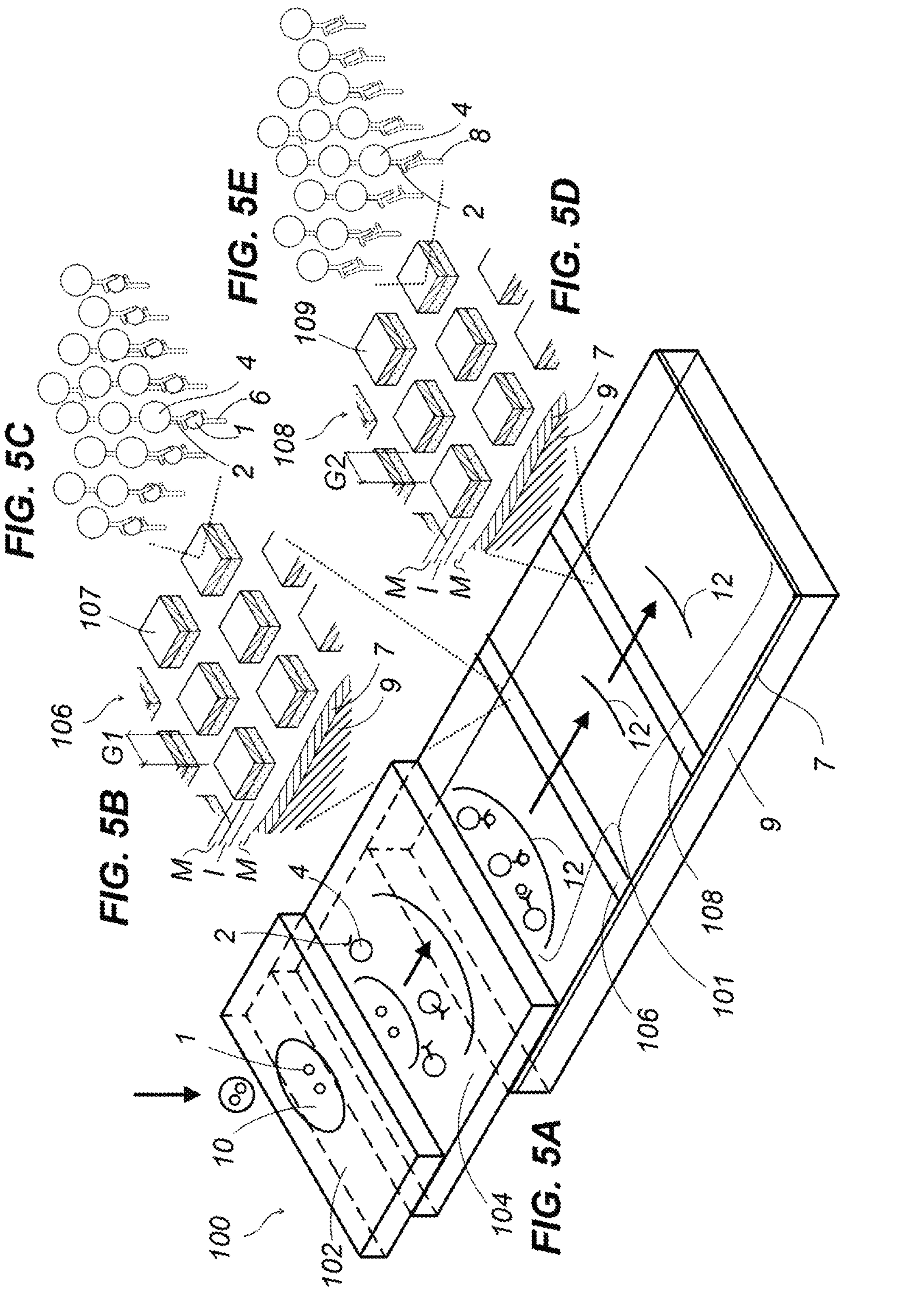
FIGS. 5A-E are a structural diagram (FIG. 5A) illustrating the overall structure of a detection device in an embodiment of the present disclosure, a medium-scale enlarged view (FIG. 5B) of a test part in the middle of a flow path, a fine-scale enlarged view (FIG. 5C) of a layer structure of islands therein, a medium-scale enlarged view (FIG. 5D) of a control part in the middle of a flow path, and a fine-scale enlarged view (FIG. 5E) of a layer structure of islands therein.

Structure Details of the MIM structure adopted in the present embodiment are described below. FIG. 5A is a structural diagram illustrating the overall structure of a detection device in the present disclosure. In the detection device 100 of the present disclosure, the metal fine particles 4, which may be fine particles labeling the reference antibody 2, and the metal thin film 7 formed on the substrate 9 that serves as the support member, form an MIM structure in the test part 106 or the control part 108 with one of the following composite layers therebetween: a composite layer of the reference antibody 2—the antigen 1—the first capture antibody 6 (for the test part 106) and a composite layer of the reference antibody 2—the second capture antibody 8 (for the control part 108). The test part 106 and the control part 108 are, for example, on a line or narrow strip that extends across the direction of flow in the flow path 101. In the flow path 101, the test part 106 is located upstream side and the control part 108 located downstream side. The substrate 9 is any member that can support the metal thin film 7 and can be an insoluble membrane carrier or any solid or gel body such as a silicon substrate, glass substrate, or resin substrate.

The sample fluid 10 is dropped into a drop site 102. When the sample fluid 10 is supplied to the drop site 102, it also permeates the conjugate section 104. In the conjugate section 104, a reference antibody 2 has been disposed in advance in a releasable manner. That reference antibody 2 is labeled with metal fine particles 4. In a real world situation, the metal fine particles 4 may be larger in size than the reference antibody 2. When the sample fluid 10 contains the antigen 1, the reference antibody 2 labeled with the metal fine particles 4 binds to the antigen 1 due to an antigen-antibody reaction. The sample fluid 12 in which conjugate of the reference antibody 2—the antigen 1 is dispersed travels through the flow path 101. The flow path 101 through which the sample fluid 12 travels is illuminated by some source of light or natural ambient light (not shown), and the reflected light is observed visually.

In the flow path 101, a metal thin film 7 is formed while supported by a substrate 9. The sample fluid 12 flows while in contact with the surface of the metal thin film 7. The metal thin film 7 may have been treated with a surface preparation or other auxiliary measures in order to properly induce chromatographic phenomena such as flowing and wetting of the sample fluid 12, as long as it does not contradict with the detection principle that will be described below. FIG. 5B is a medium-scale enlarged view of the test part 106 in the middle of the flow path 101. In the test part 106, the islands 107, whose planar shape is, for example, square are suitably arranged with a gap G1 separating them from each other. An example of this arrangement is a square lattice. The size of the islands 107 is typically about 190 nm to 420 nm square, with the width of the gap G1 is about 75 nm to 180 nm, but these sizes and shapes can be changed according to the desired color to be produced and the refractive index of the sample fluid 12. When the sample fluid 12 containing the antigen 1 passes through the island 107, an antigen-antibody reaction between the antigen 1 and the first capture antibody 6 occurs. As a result, an MIM structure is formed in which the metal thin film 7 serves as the metal (M layer), the composite layer of the first capture antibody 6—the antigen 1—the reference antibody 2 as the transparent dielectric layer (I layer), and the metal fine particles 4 as the metal (M layer). FIG. 5C is a fine-scale enlarged view of a layer structure of the islands 107. In the islands 107, the first capture antibody 6 is fixed to the surface of the metal thin film 7. The first capture antibody 6 can bind to the antigen 1 through an antigen-antibody reaction, but cannot bind to the reference antibody 2, which is not bound to an antigen 1. In order to ensure that an MIM structure is formed in the area where the islands 107 are fabricated and that no such MIM structure is formed at the gap location, the metal thin film 7 can be patterned in such a way that the first capture antibody 6 binds only to the area that corresponds to the islands 107 on the surface of the metal thin film 7. This patterning can be achieved by any techniques, such as depositing a substance that binds the first capture antibody 6 in a pattern only in the area of the islands 107.

In the area of the islands 107 before the sample fluid 12 arrives, the structure is, from the bottom side, a substrate 9, a metal thin film 7, and a first capture antibody 6, and no MIM structure is formed. The detection device 100 can be fabricated so that the test part 106 is visually indistinguishable from the portion of the flow path 101 excluding the test part 106 and the control part 108 at this stage. The same is true if the sample fluid 12 that does not contain an antigen 1 in the original sample fluid 10 arrives. In contrast, if the original sample fluid 10 contains an antigen 1, the reference antibody 2 binds to the antigen 1 in the sample fluid 12, so that the antigen 1 binds to the first capture antibody 6 and the MIM structure described above will be formed. Therefore, the MIM structure absorbs a portion of the illumination light of the wavelengths in the visible region, causing the test part 106 to produce a color.

The control part 108 has a similar structure to the test part 106, where islands 109 are formed. FIG. 5D is a medium-scale enlarged view of the control part 108 in the middle of a flow path 101. Similar to the test part 106 (FIG. 5B), the control part 108 also consists of islands 109, whose planar shape is, for example, square, spaced from each other by a gap G2, and arranged into an appropriate array of, for example, a square lattice. The typical size of the island 109 is also the same as that of the island 107, the details of which will be described below. In the islands 109, the reference antibody 2 in the sample fluid 12 forms an MIM structure with the metal thin film 7 as the metal (M layer), a composite layer of the second capture antibody 8—the reference antibody 2 as the transparent dielectric layer (I layer), and the metal fine particles 4 as the metal (M layer). FIG. 5E is a fine-scale enlarged view of a layer structure of the islands 109. Also in the islands 109, a second capture antibody 8 is fixed to the surface of the metal thin film 7. The second capture antibody 8 can bind to the reference antibody 2, which is not bound to the antigen 1 through an antigen-antibody reaction. Similar to the island 107, the MIM structure is formed where the islands 109 are fabricated. Furthermore, in order to prevent the formation of such an MIM structure at the gap position, the metal thin film 7 is patterned such that the second capture antibody 8 binds only to the area on the surface of the metal thin film 7 that corresponds to the island 109. This patterning technique can also be achieved by the same method as in the case of the islands 107.

The colors of the islands 107 in the test part 106 and of the islands 109 in the control part 108 can be adjusted by making them into a repeat pattern of islands, as described above. Therefore, the arrangement and size of the islands 109 may be matched with those of the islands 107. Alternatively, the arrangement and size of the islands 109 may be different from those for the islands 107, depending on the color to be produced or reflecting differences in the MIM structure to be formed (e.g., differences in the structure of the composite layer that serves as the I layer). Namely, the islands 107 and islands 109 may not develop exactly the same color, even if the pattern of islands, arrangement, and gap are identical, which is due to the presence or absence of an antigen 1 and the difference between the first capture antibody 6 and the second capture antibody 8. In the detection device 100, adjusting the geometry of the islands 107 and islands 109 can be easily carried out by controlling the geometry during pattern formation. As a result, it is possible to produce an identical color for the test part 106 and the control part 108, to produce different colors for the test part 106 and the control part 108, and to generate a pattern or mark on the test part 106 or the control part 108 itself instead of making the test and control parts 106, 108 into bands of identical color. Furthermore, these colors can be made more practical by selecting the color in consideration of visibility or by making the color pattern into a combination of sensitive colors, thereby lowering the detectable concentration limit of the antigen 1, increasing the accuracy of visual judgment, and improving visibility. In addition to the selection of the material of the metal fine particles 4, these color adjustments and color combination changes can be achieved by simply adjusting the geometry of the test part 106 and of the control part 108 as well as the islands 107 and islands 109 in each of those parts, while the metal fine particles 4 are unchanged.

Therefore, in this embodiment of the detection device, the optical absorption of the labeling substance of the reference antibody, such as gold nanoparticles, does not necessarily appear as it is, unlike in the conventional immunochromatography detection device. In the detection device of the present disclosure, since the absorption affected by resonance interaction of the MIM structure formed by the metal fine particles labeling the reference substance and the metal thin film on the substrate is utilized, the degree of freedom of design can be exploited to enhance the practicality of the device. Thus, in the test part 106 and the control part 108, the color difference of the device between the case where the MIM structure is formed and the case where it is not formed is visually discriminated and serves as the basis for the judgment. The presence of an antigen 1 in the analyte sample fluid 10 is sensitively detected as a change in color of the device due to the resonance absorption phenomenon of the designed metal structure. No special equipment is needed for this application. The change in color can be altered relatively freely at the design stage of the detection device and tailored so that it can be detected with sensitivity by the naked eye.

The metal fine particles 4 in an assembly function as the upper metal structure of the MIM structure, as shown in FIG. 5C and FIG. 5E. The material of the metal fine particles 4 can be determined as appropriate to achieve the desired color. Preferred materials for the metal fine particles are, for example, metals selected from the group consisting of silver, aluminum, copper, chromium, and nickel. Silver and aluminum, in particular, have the advantage over gold in that they have a high plasma frequency and no absorption bands in the visible region. Gold can also be selected for its chemical stability. These metals can also be employed for the metal thin film 7 that serves as the lower metal structure of the MIM structure. Employing these metals for the metal fine particles 4 or metal thin film 7 is advantageous to achieve the desired color. The same type of metal can be employed for the metal fine particles 4 and the metal thin film 7, or a different type of metal can be employed for the metal fine particles 4 and the metal thin film 7.

Figure 6:
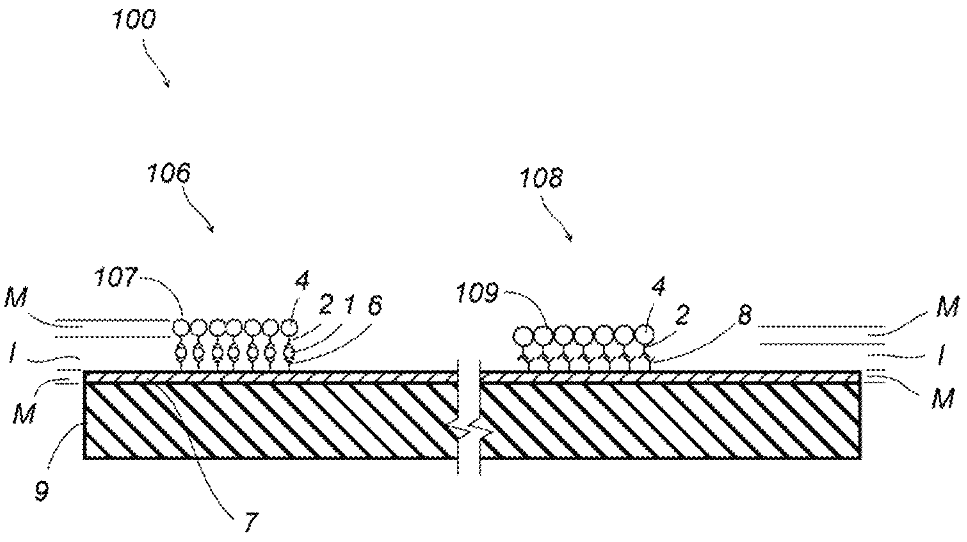
FIG. 6 is a cross-sectional view of the structure of the islands shown in FIGS. 5B and 4C in an embodiment of the present disclosure.

The geometry for adjusting the color of the MIM structure can be modified by several techniques. FIG. 6 is a cross-sectional view of the structure of the islands 107 of the test part 106 and the islands 109 of the control part 108 in the detection device 100 shown in FIGS. 5B and 4C. As shown in FIG. 6, it is the composite layer (test part 106) of the reference antibody 2, the antigen 1, and the first capture antibody 6 that forms the transparent dielectric layer (layer I) of the MIM structure. In the control part 108, the composite layer of the reference antibody 2 and the second capture antibody 8 serve as the transparent dielectric layer.

Figure 7:
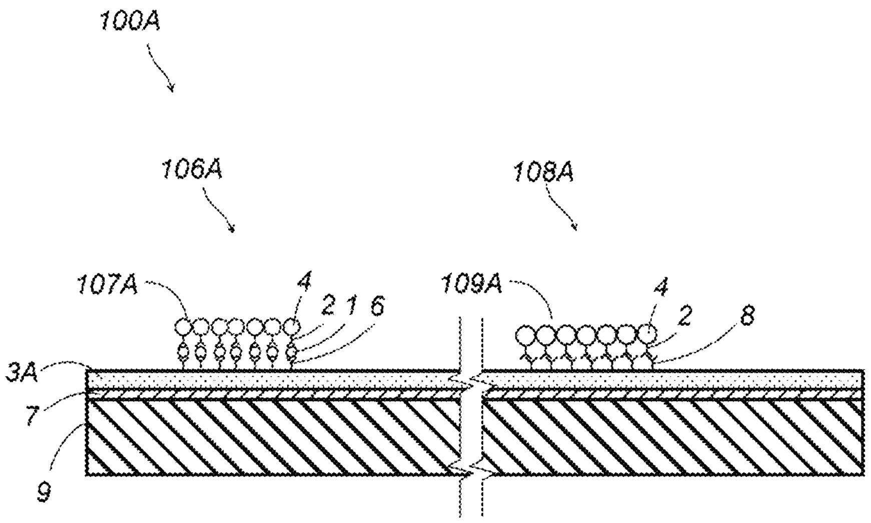
FIG. 7 is a cross-sectional view of a detection device utilizing a transparent dielectric thin film in an embodiment of the present disclosure.

For the optical operation described above, there is no particular restriction on the reference antibody 2, the first capture antibody 6, and the second capture antibody 8. The reference antibody 2, the first capture antibody 6, and the second capture antibody 8 are determined according to the target substance (antigen 1), which may be selected in consideration of an immunological reaction, a type of physicochemical binding. It follows that, it is not always possible to obtain a thickness of the transparent dielectric layer (I layer) suitable for exhibiting colors. Therefore, the detection device of this embodiment can be improved to achieve a transparent dielectric layer of a thickness that exhibits colors successfully. FIG. 7 is a cross-sectional view of the detection device 100A that utilizes a transparent dielectric thin film 3A in this embodiment. The transparent dielectric thin film 3A forms a transparent dielectric layer (I layer) of the MIM structure, together with the first capture antibody 6, the antigen 1, and the reference antibody 2. On the surface of the transparent dielectric thin film 3A, techniques for patterning are applied in the islands 107A for the test part 106A and the islands 109A for the control part 108A. The transparent dielectric thin film 3A is also formed at locations around the islands 107A and the islands 109A. The transparent dielectric thin film 3A functions as a thickness adjustment layer to make the thickness of the transparent dielectric layer (I layer) appropriate in the islands 107A and the islands 109A of the MIM structure. The transparent dielectric thin film 3A can be modified between the test part 106A and the control part 108A. Various materials can be used for the transparent dielectric thin film 3A. For example, inorganic materials such as magnesium fluoride, calcium fluoride, and silicon nitride can be used in addition to glass (silicon dioxide) and resins. Preferable materials for the transparent dielectric thin film 3A are, for example, materials that exhibit some transparency at any wavelength in the visible region.

Figure 8:
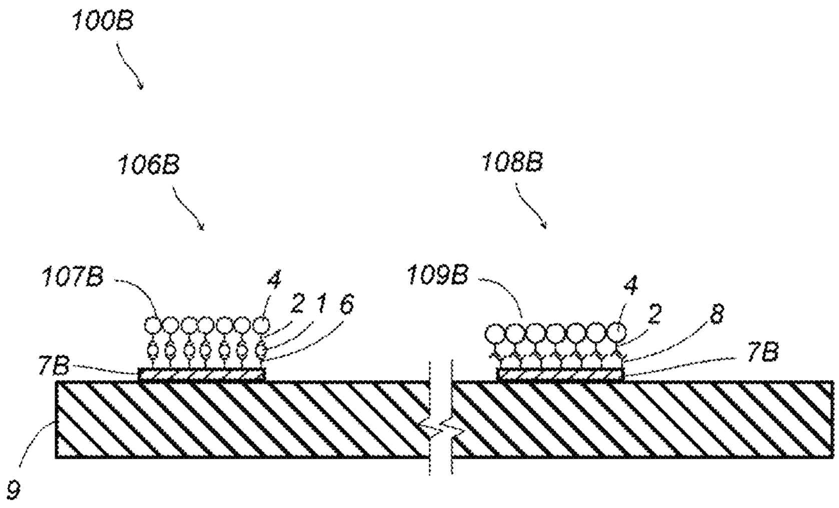
FIG. 8 is a cross-sectional view of another detection device in an embodiment of the present disclosure.

In the detection device of the present disclosure, it is also useful to pattern the metal thin film, which is the lower metal structure of the MIM structure, into a repeat pattern of islands. FIG. 8 is a cross-sectional view of another detection device 100B of this embodiment. Even if the capture antibody in the test part or control part is difficult to pattern finely for some reason, for example, the patterned lower metal thin film 7B, in which the metal thin film is patterned, can be used to adjust the color in the MIM structure. Any method adopted in microfabrication technology can be used for patterning for patterned lower metal thin film 7B formed on substrate 9. The patterned lower metal thin film 7B can be placed in islands 107B for the test part 106B, in islands 109B for control part 108B, or as needed.

Figure 9:
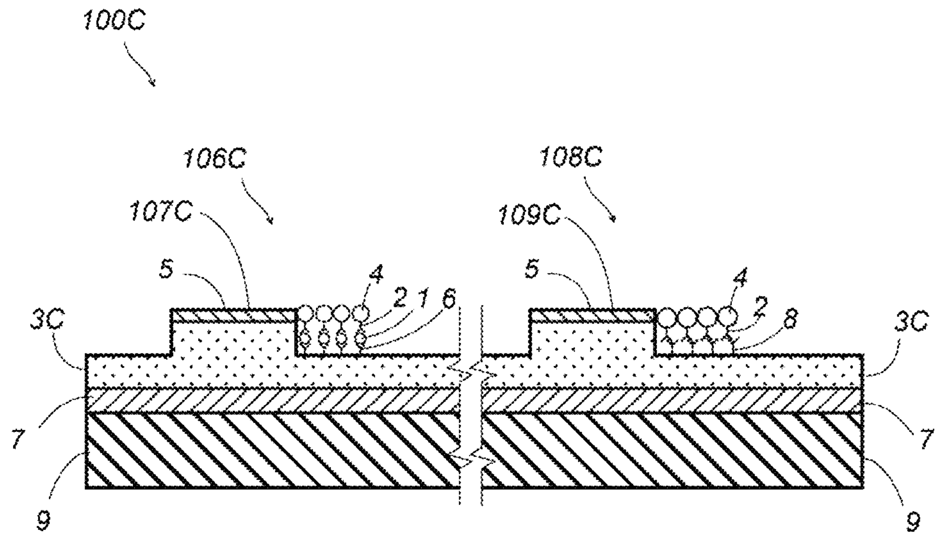
FIG. 9 is a cross-sectional view of yet another detection device in an embodiment of the present disclosure.

FIG. 9 is a cross-sectional view of yet another detection device 100C of this embodiment. The embodiment of the detection device can also have a structure of the upper metal layer for the MIM structure that utilizes an additional patterned metal thin film layer in addition to the metal fine particles. In the detection device 100C in FIG. 9, an additional metal thin film layer is placed at a position that is part of the upper metal layer of the MIM structure, which is then patterned to form the patterned upper metal thin film layer 5. In addition, the first capture antibody 6 or the second capture antibody 8 is placed at a position where the patterned upper metal thin film layer 5 is not disposed. For patterning for the patterned upper metal thin film layer 5, any techniques in fine processing technology can be used.

The transparent dielectric thin film 3C may have a step so that the area where the patterned upper metal thin film layer 5 is disposed in the detection device 100C in FIG. 9 can be thicker and the other areas can be thinner. This step can be designed according to the effective thickness of the composite layer having the reference antibody 2, antigen 1, the first capture antibody 6, and the second capture antibody 8. This step also can be fabricated by fine processing techniques. Furthermore, the transparent dielectric thin film 3C can be single or multilayered. In the case it is multilayered, the step can be easily adjusted by stacking layers that have different etching rates. In addition, the transparent dielectric thin film 3C can be formed only in the area where the patterned upper metal thin film layer 5 is disposed. The metal fine particles 4 patterned upper metal thin film layer 5 can be disposed on both or either of the test part 106C and control part 108C as needed.

In the detection devices 100, 100A, and 100B in FIGS. 5-8, the upper metal layers of the MIM structures are comprised of metal fine particles 4 that can be disposed by way of the function of the capture antibodies 6 and 8. In that case, change in color exhibited at the test part and control part depending on the presence or absence of the metal fine particles 4 is utilized. For example, in the detection device 100 of FIG. 5, the observed color of the test part 106 illuminated by white light is white for a sample fluid 10 that does not contain an antigen 1, and not white for a sample fluid 10 that contains an antigen 1 and forms an MIM structure due to the presence of metal fine particles 4. In contrast, in the test part 106C and the control part 108C of the detection device 100C in FIG. 9, the islands 107C form an MIM structure due to the patterned upper metal thin film layer 5 even when there were no metal fine particles 4. When the sample fluid 10 contains the antigen 1 and is supplied with metal fine particles 4, both the metal fine particles 4 and the patterned upper metal thin film layer 5 serve as the upper metal layer of the MIM structure, which changes the effective size of that upper metal layer and changing its color. In this embodiment, the shape and size of the islands 107C and islands 109C, including the patterned upper metal thin film layer 5, can be designed so that the change in color can be easily observed visually. In other words, the observed color can be configured to be a non-white color (color A) for the sample fluid 10 that does not contain an antigen 1, and a different non-white color (color B) for the sample fluid 10 that contains an antigen 1 and forms an MIM structure due to the presence of metal fine particles 4. In the detection device 100C, the presence or absence of metal fine particles 4 changes the size of the upper metal layer of the MIM structure, and thus can cause the change in color.

3. EXPERIMENTAL VERIFICATION

The color production phenomenon expected for the islands 109 of the control part 108 in FIG. 6 of this embodiment has been verified experimentally. FIG. 10A is a schematic cross-sectional view illustrating the conditions for this verification, FIG. 10B is an SEM photograph of the gold pattern formed actually, and FIGS. 10C and 10D are optical microscope images before and after dropping the sample fluid. As shown in FIG. 10*a*, a silicon wafer was employed for the substrate 9, the surface of which was coated with aluminum with a thickness of 100 nm. On top of the aluminum, a square lattice of gold circular patch array structure with a film thickness of 5 nm, a diameter of 100 nm, and a pitch of 200 nm was fabricated. The aluminum corresponded to the metal thin film 7, and the gold circular patch array structure was coated to selectively modify biotin molecules, which will be described below. Experimental verification has also been performed based on a circular pattern, though the islands 109 in FIG. 6 form a square pattern. As shown in FIG. 10B, each circular patch was generally 100 nm in diameter. The gold circular patch array structure was formed only in an area of 800 μm square.

The area of the gold circular patch array structure at this stage was visually indistinguishable from the surrounding areas where no gold patches were formed. In other words, even if the gold patch structure is exposed to air or a refractive index medium (such as water) is placed over it, the presence of the gold patch remains achromatic and exhibits only a very slight change in brightness, just like its surroundings, as indicated by the range in FIG. 10C, which makes it almost impossible to discern visually. This is because the gold film thickness of the gold patch is as thin as 5 nm, and the optical effects such as color rendition characteristic to gold hardly appear.

Next, the substrate surface was modified with biotin molecules. Biotin molecules bind only to the circular patch of gold and serves as the second capture antibody 8 (FIG. 6) in the MIM structure. At this stage, the region of the gold circular patch array structure was still visually indistinguishable from the surrounding areas where no gold patches were formed.

As a liquid corresponding to the sample fluid 10, a dispersion liquid of gold nanoparticles with a diameter of 50 nm whose surface was modified with avidin was prepared. In the MIM structure, avidin serves as the reference substance (reference antibody 2) labeled by the gold nanoparticles of this embodiment. This dispersion liquid was dropped onto the area covering the portion of the substrate surface where the above circular patch of gold was formed, letting it react. Then, only the area where the circular gold patch was formed turned pink in color, while the area where the gold circular patch was not formed remained the same achromatic gray color as before. FIG. 10D shows this situation. FIG. 10D is a black-and-white reproduction of the color photograph, and the area that is pink in the color photograph (the central square area where the range is indicated) is shown only as a gray color with lower brightness than the surrounding area.

The inventor of this application believes that this color production phenomenon occurred as follows: the biotin and avidin molecules combined in the area where the gold circular patch was formed, which results in the formation of an MIM structure having a gold nanoparticle layer (M layer) labeling the avidin molecule, a composite layer of avidin and biotin molecules (I layer), and a metal layer (M layer) of an aluminum thin film and the gold circular patch area, while the MIM structure was patterned.

These series of experiments have revealed that it is possible to visually determine whether or not the MIM structure is actually formed in the control part 108 in FIG. 6. Since there is every reason to expect that the MIM structure can be formed in the same way also in the islands 107 of the test part 106 through an antigen-antibody reaction, the inventor believes that the principle of operation of the detection device 100 in this embodiment was experimentally proven. In addition, the inventor believes that the general method of artificially designing colors by adjusting geometry and materials separately developed by the inventor (Patent Document 2) can be applied to this embodiment as well.

4. VARIATIONS

In the explanation above, we have focused on the optical behavior at the test part and control part, which serve as the detection part. In order to facilitate visual detection and to increase sensitivity, the flow path 101 can be structured to facilitate judgment at the detection section as well as at other locations in the flow path 101, including other sites than the detection section. For example, by forming the patterned upper metal thin film layer 5 shown in FIG. 9 even at positions other than the detection section, the background colors of the flow path 101 can be adjusted by the MIM structure. The colors produced in the case the metal fine particles 4 are disposed in the test part 106 and the control part 108 can be adjusted to another designed colors that can be easily contrasted with background colors. The detection device of this embodiment allows for easy adjustment of the color in such a flexible way.

The above description has assumed a structure in which the target substance is an antigen, the reference substance is a reference antibody capable of physicochemically binding to that antigen, and the capture substance is a capture antibody capable of physicochemically binding to at least one of that antigen or that reference antibody. This embodiment of the detection device can also be employed for immunological testing with other combinations. That is, it can be implemented by having the target substance being an antibody, the reference substance being a reference antigen capable physicochemically binding to that antibody, and the capture substance being a capture antigen capable of physicochemically binding to at least one of that antibody or that reference antigen. The same can also be applied to molecules that identify and bind to each other.

5. CONCLUSION

The embodiments of the present disclosure have been described in detail above. Each of the above embodiments and structure examples are described to illustrate the disclosure, and the scope of the disclosure of this application should be determined based on the claims. Variations that exist within the scope of this disclosure, including other combinations of each embodiment, are also included in the claims.

INDUSTRIAL APPLICABILITY

The disclosure is utilized in the manufacture of detection devices for testing applications in which physicochemical binding, including immunological reactions, is used to determine the presence or absence of a target substance.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A detection device for detecting a target substance that may be contained in a sample fluid, comprising:
- a flow path for the sample fluid to which a reference substance is dispersed, the reference substance being capable of physicochemically binding to the target substance; and
- at least one detection part disposed in the flow path, the detection part being visible and having a capture substance fixed to at least part of a contact surface thereof,
- wherein the reference substance is labeled by fine particles,
- wherein the capture substance can bind physicochemically to at least one of the target substance that is bound to the reference substance, or to the reference substance,
- wherein the fine particles form an assembly along the contact surface and produce a color, the assembly being formed by the physicochemical binding of the target substance, which binds to at least one of the reference substance and the capture substance, or the physicochemical binding of the reference substance to the capture substance,
- wherein the fine particles are metal fine particles,
- wherein the at least one detection part has a metal thin film formed on a support member,
- wherein the at least one detection part is configured to form a metal-insulator-metal (MIM) structure when the target substance is contained in the sample fluid, the MIM structure including:
  - the metal thin film;
  - at least one of a composite layer of the capture substance, the target substance, and the reference substance, or a composite layer of the capture substance and the reference substance; and
  - an assembly of the metal fine particles,
- wherein the at least one detection part includes a test part provided in an upstream side of the flow path and a control part provided in a downstream side of the flow path,
- wherein the test part has a first capture substance for the capture substance of the test part, the first capture substance fixed to a surface contacting the sample fluid,
- wherein the control part has a second capture substance for the capture substance of the control part, the second capture substance fixed to a surface contacting the sample fluid,
- wherein the MIM structure in the test part includes the metal thin film, a composite layer of the first capture substance, the target substance, and the reference substance, and an assembly of the metal fine particles, and
- wherein the MIM structure in the control part consists of the metal thin film, a composite layer of the second capture substance and the reference substance, and an assembly of the metal fine particles.

2. The detection device according to claim 1, wherein a color of the MIM structure in the detection part is adjusted by patterning the capture substance into a repeat pattern of islands.

3. The detection device according to claim 1,
- wherein a color of the MIM structure in the detection part is adjusted by patterning the metal thin film into a repeat pattern of islands.

4. The detection device according to claim 2, wherein the repeat pattern of islands is a pattern of islands with islands spaced apart with each other, the pattern of islands having at least one shape selected from the group consisting of shapes of substantial squares, substantial circles, and substantial rectangles.

5. The detection device according to claim 1,
- wherein the metal fine particles are fine particles that contain one of metals selected from the group consisting of silver, aluminum, copper, chromium, and nickel.

6. The detection device according to claim 1, further comprising a thickness adjustment layer of transparent dielectric media on the metal thin film in the detection part, wherein the capture substance is disposed on the thickness adjustment layer.

7. The detection device according to claim 1, further comprising in the detection part:
- a transparent dielectric thin film disposed on the metal thin film; and
- an additional metal thin film layer that is patterned and disposed on the transparent dielectric thin film,
- wherein the capture substance is disposed in a location where the additional metal thin film layer is not disposed.

8. The detection device according to claim 1, wherein the fine particles are semiconductor fine particles.

9. The detection device according to claim 8, wherein the semiconductor fine particles contain one of the semiconductor materials selected from the group consisting of silicon (Si), germanium (Ge), and gallium (Ga).

10. The detection device according to claim 1, wherein the fine particles are compound fine particles.

11. The detection device according to claim 10, wherein the compound fine particles contain any one compound selected from the group consisting of titanium nitride (TiN), silicon carbide (SiC), gallium nitride (GaN), hafnium sulfide ($HfS_2$), zinc sulfide (ZnS), barium titanate ($BaTiO_3$), and vanadium dioxide ($VO_2$).

12. The detection device according to claim 1,
wherein the target substance is an antigen,
wherein the reference substance is a reference antibody capable of physicochemically binding to the antigen, and
wherein the capture substance is a capture antibody capable of physicochemically binding at least either to the antigen or to the reference antibody.

13. The detection device according to claim 1,
wherein the target substance is an antibody,
wherein the reference substance is a reference antigen capable of physicochemically binding to the antibody, and
wherein the capture substance is a capture antigen capable of physicochemically binding at least either to the antibody or to the reference antigen.

14. A detection device for detecting a target substance that may be contained in a sample fluid, comprising:
a flow path for the sample fluid to which a reference substance is dispersed, the reference substance being capable of physicochemically binding to the target substance; and
at least one detection part disposed in the flow path, the detection part being visible and having a capture substance fixed to at least part of a contact surface thereof,
wherein the reference substance is labeled by fine particles,
wherein the capture substance can bind physicochemically to at least one of the target substance that is bound to the reference substance, or to the reference substance,
wherein the fine particles form an assembly along the contact surface and produce a color, the assembly being formed by the physicochemical binding of the target substance, which binds to at least one of the reference substance and the capture substance, or the physicochemical binding of the reference substance to the capture substance,
wherein the fine particles are metal fine particles,
wherein the at least one detection part has a metal thin film formed on a support member,
wherein the at least one detection part is configured to form a metal-insulator-metal (MIM) structure when the target substance is contained in the sample fluid, the MIM structure including:
the metal thin film;
at least one of a composite layer of the capture substance, the target substance, and the reference substance, or a composite layer of the capture substance and the reference substance; and
an assembly of the metal fine particles, and
wherein the at least one detection part further comprises:
a transparent dielectric thin film disposed on the metal thin film; and
an additional metal thin film layer that is patterned and disposed on the transparent dielectric thin film,
wherein the capture substance is disposed in a location where the additional metal thin film layer is not disposed.

* * * * *